US00PP09263P

United States Patent [19]

Pollok

[11] Patent Number: Plant 9,263

[45] Date of Patent: Aug. 29, 1995

[54] NECTARINE TREE — 'POLLOK' CULTIVAR

[75] Inventor: Zenith E. Pollok, Mason, Mich.

[73] Assignee: Stark Brothers Nurseries and Orchards Company, Louisiana, Mo.

[21] Appl. No.: 348,177

[22] Filed: Nov. 28, 1994

[51] Int. Cl.[6] ..... A01H 5/00
[52] U.S. Cl. ..... Plt./413
[58] Field of Search ..... Plt. 41.3

*Primary Examiner*—James R. Feyrer
*Attorney, Agent, or Firm*—Burns, Doane, Swecker & Mathis

[57] ABSTRACT

A new and distinct nectarine tree named Pollok is provided. The new cultivar originated from an open-pollinated peach seed of unknown parentage that was planted by the originator during 1978 or 1979. The new variety is a consistent producer of attractive moderately large freestone fruit with a high degree of bright red skin coloration which ripens late in the commercial nectarine harvest season of the Eastern United States. Firm highly-flavored moderately acidic yellow fruit flesh of excellent quality is formed having only a slight amount of red tinging. The growth habit is moderately vigorous. The firmness of the fruit flesh renders it well amenable for shipment to consumers.

2 Drawing Sheets

SUMMARY OF THE INVENTION

The present invention comprises a new and distinct nectarine cultivar that originated as a chance seedling. The originator of the new cultivar planted a number of open-pollinated peach pits of unknown parentage in his backyard at Mason, Mich. during 1978 or 1979. The new cultivar was selected from one of the resulting trees. Fruit was first observed on a single tree of the new cultivar during September, 1984, and was remarkable for its lateness of harvest and attractive appearance. Had the originator not discovered and preserved the original plant of the new cultivar it would have been lost to mankind.

It was found that the new nectarine tree of the present invention:

(a) consistently forms attractive late-maturing fruit having a moderately large size wherein approximately 60 to 90 percent of the skin is bright red in coloration at the time of harvest,
(b) forms a firm highly-flavored yellow freestone fruit flesh of excellent quality having only a slight amount of red tinging,
(c) exhibits a moderately vigorous growth habit, and
(d) exhibits cold hardiness, resistance to bacterial leafspot, and resistance to trunk canker that is at least as great as that of Redgold and Sunglo cultivars (each non-patented in the United States).

The late maturity of the fruit of the new cultivar is considered to be particularly significant. In recent years a large volume of fresh stone fruit is distributed through North American trade channels from about mid-July to about mid-August. Information presented by packers and shippers at the 1994 Mid-Atlantic Tri-State Regional Horticultural Society meeting held during February, 1994, at Martinsburg, W. Va., indicated that peaches and nectarines of adequate size and quality, ripening after the aforementioned main harvest season should enjoy ready marketability and potentially higher prices than the fruit commonly produced during the main harvest season. The ability to harvest high quality nectarines in the Eastern United States during late August and early September having satisfactory characteristics is considered to present an attractive alternative fruit crop for growers. The new cultivar of the present invention is believed to be well suited to meet this heretofore unfilled need of the nectarine industry and reliably provides a quality fruit harvest at a time when other cultivars of the same or similar size, color and quality are already past fruit production. When grown near Kelso, Mo., the fruit of the new cultivar commonly is ready for commercial harvest from approximately August 20th to approximately September 1st. Such harvest time is approximately 36 to 38 days after that of the well-known Redhaven peach (non-patented in the United States).

It has been found that the new cultivar exhibits good or better tolerance to bacterial leafspot caused by *Xanthomonas pruni* as other main-season nectarine cultivars such as Redgold, Sunglo, and Fantasia (each non-patented in the United States). The bud-hardiness during field observations in Southeastern Missouri has been sufficient to provide a heavy return bloom in four out of the five seasons it has been observed. The flavor of the fruit is excellent. Also, the firmness of the fruit makes it well suited for commercial harvest and for shipping to local and/or regional markets.

Beginning in 1985 trees of the new variety have been grafted onto Lovell seedling rootstock at Louisiana, Mo. Trees were allowed to grow following grafting during the 1986 growing season, were dug in the Fall of 1986, and were planted in the Spring of 1987 in Block No. 2 of the Test Orchard of Stark Brothers Nurseries and Orchards Company at Kelso, Mo. Fruit was first observed in this Test Orchard during the 1989 season. Throughout observations over a number of years it has been confirmed that the characteristics of the new cultivar are firmly fixed and are reliably transmitted to succeeding generations following such asexual reproduction.

The new cultivar of the present invention has been named the Pollok cultivar, and is being marketed by the Stark Brothers Nurseries and Orchards Company of Louisiana, Mo., under the Stark and Ovation trademarks.

BRIEF DESCRIPTION OF THE PHOTOGRAPHS

The accompanying photographs show specimens of the new cultivar as depicted in color as nearly true as it is reasonably possible to make the same in color illustrations photographs of this type. All specimens were obtained from first generation budded trees of the new Pollok cultivar while present on Lovell rootstock growing in Block No. 2 of the Prunus sp. Test Orchard of Stark Brothers Nurseries and Orchards Company located near Kelso, Mo. The aforementioned block was managed during the 1994 season with only a minimal maintenance spray program thereby making it difficult to obtain blemish-free fruit. Any fruit blemishes that are visible in the photographs should be considered to be the result of this minimal maintenance effort and should not be attributed to any fault of the new cultivar.

FIG. 1 illustrates typical bloom, mature trunk, and bark of the new nectarine cultivar as grown near Kelso, Mo. The photograph was taken on Apr. 2, 1994.

FIG. 2 illustrates the typical foliage and mature fruit appearance of the new nectarine cultivar when harvested on Aug. 8, 1994 wherein there is presented a fruit showing the side at right angles to the suture plane (i.e., at the top), a fruit showing the bottom of the fruit (i.e., at the bottom), and two halves of a fruit divided along the suture plane showing the flesh color, stone, and stone freeness (i.e., at the middle). The photograph was taken on Aug. 19, 1994.

FIG. 3 illustrates typical mature fruit of the new nectarine cultivar of the present invention harvested on Aug. 18, 1994, showing views of the basal end, the apical end, the two sides of a transverse section of a single fruit, two fruit from the sun-exposed sides perpendicular to the suture planes, and two sides of a longitudinal section of a single fruit. The photograph was taken Aug. 29, 1994.

DETAILED DESCRIPTION

Figure 1:
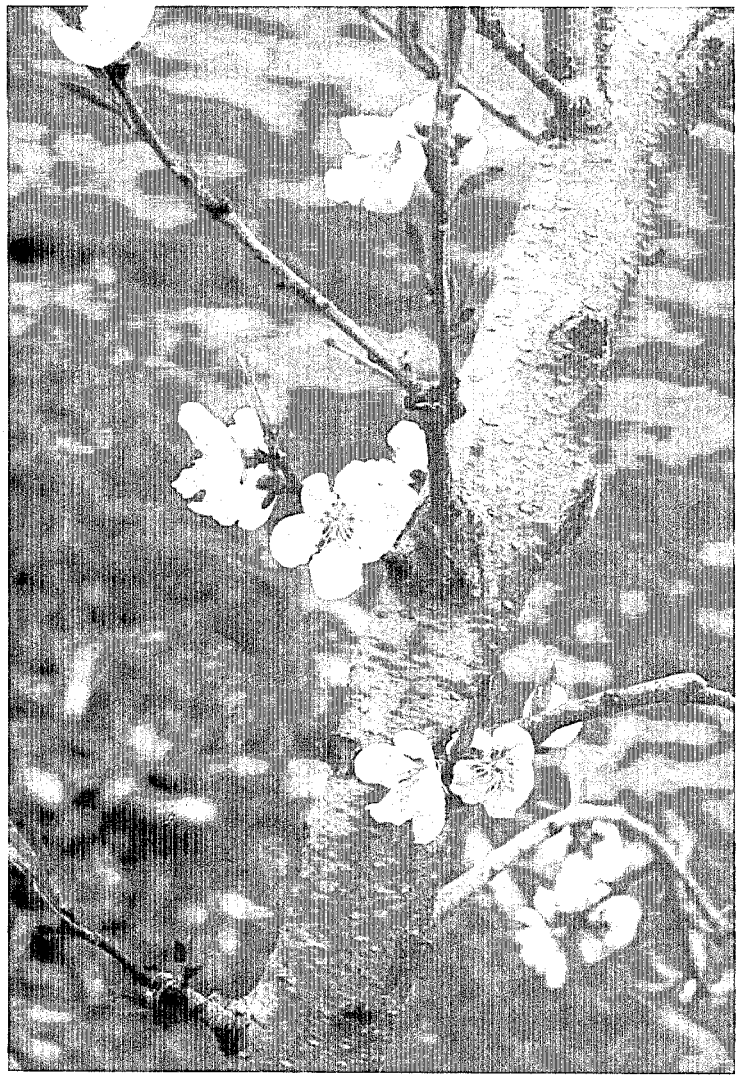
Figure 2:
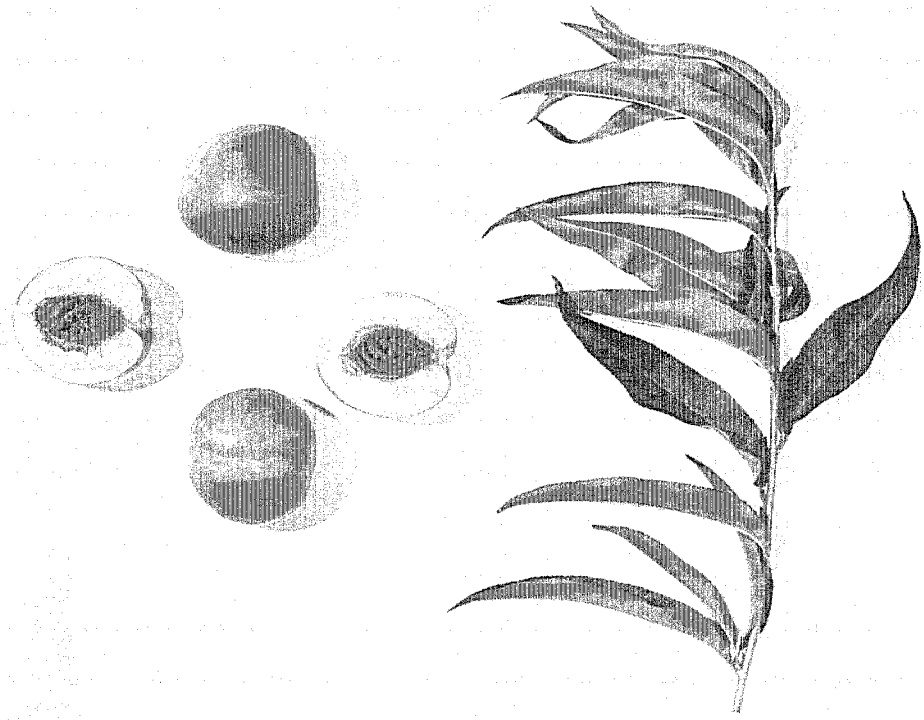
Figure 3:
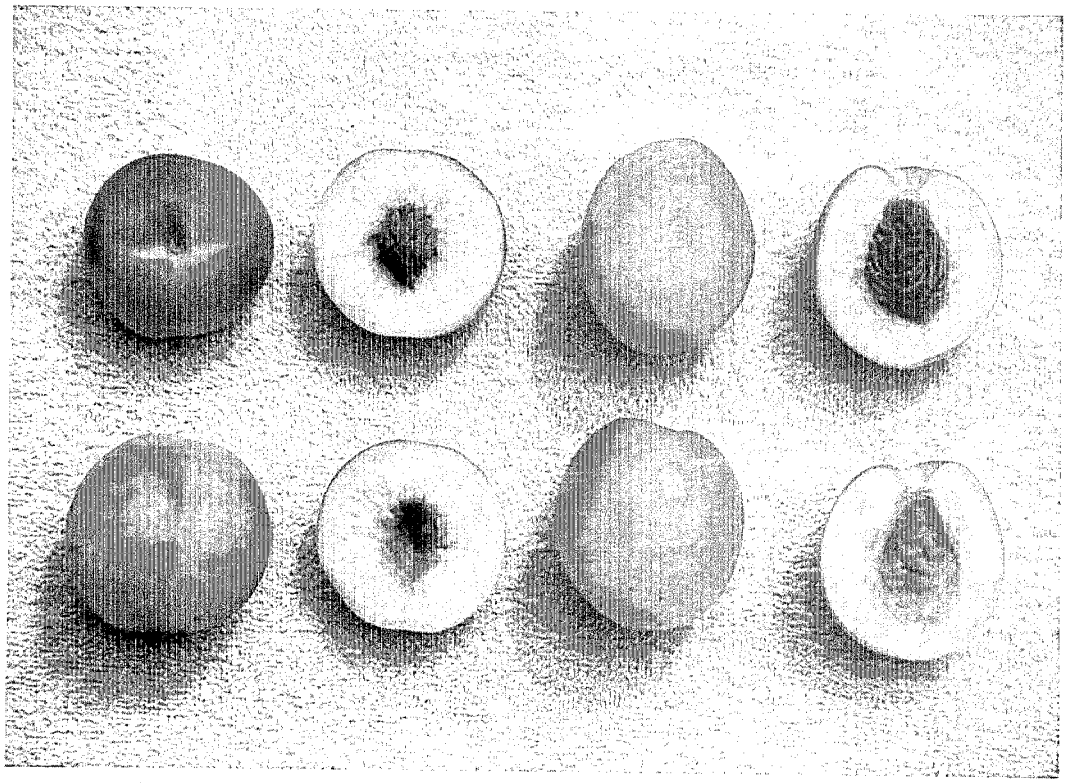

The following is a detailed description of the new cultivar that is based upon the observation of trees grown and fruit harvested from the previously-identified Test Orchard near Kelso, Mo. Color designations are presented while using the R.H.S. Colour Chart of The Royal Horticultural Society, London, England.

TREE

Size: Moderately vigorous.

Growth habit: Spreading and semi-upright, moderate frequency of branching, and commonly forming branch angles of approximately 60 to 90 degrees.

Productivity: Heavy, based upon the observation of five years of fruiting.

Cropping: Consistent.

Trunk:

- *Diameter.*—Medium large.
- *Surface characteristics.*—Smooth with intermittent fissuring and conspicuous lenticals.
- *Color.*—Gray Group 201A.
- *Lenticels.*—Erumpant, and approximately 2.0 mm.×6.0 mm.

Branches:

- *Diameter.*—Slightly more slender than average.
- *Four year old.*—Surface texture: Smooth with occasional fissures and conspicuous lenticels. Color: Grey-Brown Group 199A. Lenticels: Erumpant. Color: Greyed-Orange Group 165B.
- *Three years old.*—Surface texture: Smooth with conspicuous lenticels. Color: Grey-Brown Group 199C. Lenticels: Erumpant. Ranging in size from approximately 1.0 mm to 1.5 mm. in width and approximately 2.0 to 3.0 mm. in length. Color: Greyed-Orange Group 165B.
- *Two years old.*—Surface texture: Smooth with conspicuous lenticels and lighter-colored horizontal striations. Color: Greyed-Orange Group 165A. Lenticels: Numerous. Ranging in size from less than approximately 1.0 mm. to approximately 1.5 mm. in width and approximately 1.5 to 2.3 mm. in length. Color: Greyed-Orange Group 165B to Greyed-Orange Group 172D.
- *Current season.*—Surface texture: Glabrous. Color: Yellow-Green Group 144B with a sun-exposed ventral surface of Greyed-Red Group 181B. Lenticels: Inconspicuous.

Leaves:

- *Size.*—Medium.
- *Length of mature leaves on current season's growth.*—Commonly ranges from approximately 5.1 inches (13.0 cm.) to approximately 7.5 inches (19.1 cm). Commonly averages approximately 6.4 inches (16.3 cm).
- *Width of mature leaves on current season's growth.*—Commonly ranges approximately from 1.1 inch (2.8 cm.) to approximately 2.0 inches (5.1 cm). Commonly averages approximately 1.5 inch (3.8 cm).
- *Shape.*—Lanceolate.
- *Marginal form.*—Simply serrated and occasionally compoundly serrate.
- *Color.*—Upper: Green Group 137A. Lower: Yellow-Green Group 147B.
- *Petiole.*—Length on current season's growth: Commonly averages approximately 7/16 inch (1.11 cm.). Width on current season's growth: Commonly averages approximately 1/16 inch (0.16 cm.). Color: Yellow-Green Group 144D to Yellow-Green Group 151A. Glands: Frequently alternate and occasionally opposite on either side of petiole and on leaf blade margin at base. Number: Commonly averages three with two on the petiole and one on the basel margin of the leaf blade. Size: Large, commonly up to approximately 1/16 inch in length. Shape: Reinform with raised lips on the short side, and very occasionally globose.

Ripe current season flower buds:

- *Size.*—Small.
- *Shape.*—Round in transverse cross-section, and ovoid in axial cross-section.
- *Color.*—Brown Group 200B to 200C.

Flowers:

- *Timing of bloom.*—Moderately late. Approximately March 30th to April 5th at stated location.
- *Size.*—Large.
- *Corolla.*—Approximately 33 to 38 mm. in width at anthesis.
- *Petals.*—Approximately 13 to 15 mm. in width and approximately 16 to 18 mm. in length.
- *Type.*—Showy.
- *Color.*—Pink to pale pink with deeper, more intense color in the center and basal portion of the petals. Ranging from Red-Purple Group 63C at the darkest and Red-Purple Group 62B and 65A at the lightest.

*Styles.*—40 to 42 in number.

*Color.*—The bases tend to be darker than the remainder of the petals, Red-Purple Group 64B and Red-Purple Group 63B near the distal end.

FRUIT

Maturity: Normally ready for commercial harvest from August 20th to September 1st near Kelso, Mo. This is approximately 36 to 38 days after the Redhaven peach.

Size: Moderately large.

*Axial diameter.*—Commonly averages approximately 2¾ inches (7.0 cm) and ranging up to approximately 3 inches (7.6 cm.).

*Transverse diameter in suture plane.*—Commonly averages 2½ inches (6.4 cm.) and ranging up to 3 inches (7.6 cm).

*Transverse diameter at right angle to suture plane.*—Commonly averages 2⅝ inches (6.7 cm.) and ranging up to 2¾ inches (7.0 cm).

Form: Ranging from ovoid to slightly oblong and necked, occasionally globose, and the halves are slightly unequal in size and unsymmetrical. The basel end commonly is raised on both sides on the ventral edge and above both sides on dorsal edge by approximately ¼ to ⅜ inch (0.6 cm to 1.0 cm.). Is slightly compressed transversely in the suture plane (e.g., ⅛ inch or 0.3 cm).

*Suture.*—Distinct, smooth, and shallow (maximum depression is approximately ⅛ inch or 0.3 cm.). The maximum depression is on ventral surface (suture side) near the apex. Commonly extends from the base to the apex on the ventral surface. Very slightly depressed to flat on the ventral surface near base (stem-end). Non-lipped.

*Ventral surface.*—Conspicuous. Extending from base to apex. Very slightly depressed to flat. Commonly has a slightly marked depression on the dorsal side of the pistil point. Is marked by moderate longitudinal striping in the overcolor. Non-lipped.

*Stem cavity.*—Flaring. Slightly elongated in the suture plane with the suture being slightly depressed on both sides.

*Depth.*—Approximately 5/16 inch (0.3 cm.).

*Width in suture plane.*—Approximately 1 inch (2.5 cm.).

*Width at right angle to suture plane.*—Approximately 13/16 inch (2.1 cm.).

*Apex.*—Rounded and mammiform.

*Base.*—Narrow and abruptly truncated at angles to the axial diameter and the transverse diameter in suture plane, with shoulders. The shoulder is raised on both sides of the ventral surface above the dorsal surface.

*Pistil point.*—Depressed. The tip is small, brown, cuneate, apical, and firmly attached.

Stem:

*Size.*—Length is approximately ¼ (0.6 cm.), and approximately ⅛ inch (0.3 cm.) in caliper. Glabrous surface. Only moderate adherence to the stone when harvested commercially ripe. Readily abscises when eating ripe.

Skin:

*Surface texture.*—Glabrous with no waxy cuticle.

*Adhesion.*—Only moderate tenacity to flesh.

*Tendency to crack.*—None.

*Pubescence.*—None.

*Color.*—Bright red over approximately 60 to 90 percent of the skin at time of harvest, Red Group 46A to Red Group 53A. Where lightly speckled over ground color, Red Group 46C, and Greyed-Purple Group 187A on the most highly exposed surfaces. The color pattern is washed to highly splashed.

*Ground color.*—At commercial harvest Yellow-Orange Group 22B. At eating ripe Yellow-Orange Group 22A.

*Lenticels.*—Inconspicuous.

Flesh:

*Color.*—Yellow-Orange Group 20A. Mostly clear yellow with no speckling. Very slightly, occasional red tinge in flesh within approximately ⅛ inch (0.3 cm.) to approximately ¼ inch (0.6 cm.) of the pit cavity, Greyed-Purple Group 185A. On highly sun-exposed fruit surfaces, occasional faint, scattered red speckling in the flesh radiating out from the pit cavity towards the highly sun-exposed surface. Only a small proportion of the flesh possesses red coloration.

*Surface of stone cavity.*—Rough with few a short fibers.

*Color of the stone cavity.*—Faintly purple, Greyed-Purple Group 185B.

*Juice.*—Rich and abundant. Mildly acid.

*Texture.*—Firm and crisp when harvested. Meaty, buttery, and melting when eating-ripe.

*Fibers.*—Few, fine, and inconspicuous.

*Ripening.*—Can be harvested in two commercial pickings.

*Flavor.*—Acid content is mild to moderate, rich and full-flavored, excellent in taste.

*Aroma.*—Pronounced.

*Eating quality.*—Best.

Stone:

*Type.*—Free from flesh.

*Fibers.*—Medium in length, and retain some short fiber-like threads in some pits and furrows.

*Size.*—Medium to large.

*Axial length.*—Commonly average approximately 1.7 inch (4.3 cm.).

*Transverse width in suture plane.*—Commonly average 1.1 inch (2.8 cm.).

*Transverse thickness at right angle to suture plane.*—Commonly average 0.8 inch (2.0 cm.).

*Form.*—Strongly obovoid and necked.

*Apex.*—Acute, and cuneate.

*Base.*—Oblique, narrow, and oblong.

*Stem adhesion surface.*—Small, elliptical, elongated in suture plane, approximately ⅛ inch by approximately ¼ inch in diameter (0.3 cm. by 0.6 cm.) and furrowed.

*Sides.*—Equal, somewhat flattened at right angles to the suture plane, and slightly curved toward the ventral surface of fruit (suture side).

*Surface.*—Possesses axially oriented furrows separated from side furrows along the ventral edge from the base to the apex. Pitted on sides near the base to ⅓ of the way up the fruit towards the apex. More finely pitted on top of the ridges towards the apex to ⅓ of the way down the stone towards the base. Irregularly furrowed on apical ⅔ of stone. Pitted from the base to ⅓ of the way up stone towards the apex.

*Ridges.*—Ragged ridge apices towards the ventral edge of the stone with rounded ridge apices on sides and towards dorsal edge.

*Pits.*—Elongated to occasionally rounded.

*Dorsal edge.*—Full, with deep, narrow groove from base to $\frac{2}{3}$ of the way up the stone towards the apex. The remaining $\frac{1}{3}$ commonly tends to be narrow and shallow. Ridges on either side are interrupted within $\frac{1}{4}$ inch of the dorsal groove.

*Ventral edge.*—Moderately thick to thick without wings.

*Color.*—The tops of ridge are Greyed-Orange Group 174A to Greyed-Orange Group 177B, and the basal $\frac{1}{2}$ of the stones are Greyed-Purple Group 183A.

*Surface of pit cavity.*—Smooth, Greyed-Orange Group 166C.

*Pit.*—Normal texture. On basal area there commonly is a light-colored portion between veins of Greyed-Orange Group 164A to Greyed-Orange Group 172C. The veins and apex commonly are Greyed-Orange Group 175A.

Use: Commercial fresh market, dessert, and culinary.

Keeping Quality: Good. Fruit has kept in cold storage from three to four weeks without noticeable deterioration.

Resistance to Insects: Comparable to other commercial nectarine cultivars grown in the Eastern United States when tested side-by-side with the new cultivar near Kelso, Mo.

Resistance to Diseases: Tolerance to bacterial leaf spot is as good or slightly better than that of the Redgold and Sunglo cultivars. More resistant to trunk cankering than the Redgold and Sunglo cultivars as observed in the field in an eight year-old side-by-side planting near Kelso, Mo.

Shipping Quality: Good to excellent due to firm flesh at harvest and the tenacity of the skin to the flesh.

Although the new variety of nectarine tree possesses the above described characteristics as a result of the growing conditions near Kelso, Mo., it is to be expected that variations of the usual type and magnitude may appear that are caused by differences in growing conditions, fertilization, pruning, pest control, and other horticultural practices when the new cultivar is grown in different environments.

I claim:

1. A new and distinct nectarine cultivar having the following combination of characteristics:

(a) consistently forms attractive late-maturing fruit having a moderately large size wherein approximately 60 to 90 percent of the skin is bright red in coloration at the time of harvest, (b) forms a firm highly-flavored yellow freestone fruit flesh of excellent quality having only a slight amount of red tinging, (c) exhibits a moderately vigorous growth habit, and (d) exhibits cold hardiness, resistance to bacterial leaf-spot, and resistance to trunk canker that is at least as great as that exhibited by the Redgold and Sunglo cultivars;

substantially as herein shown and described.

* * * * *